(12) United States Patent
Jiao et al.

(10) Patent No.: US 11,493,479 B2
(45) Date of Patent: Nov. 8, 2022

(54) LOW-FREQUENCY ELECTROMAGNETIC DETECTION METHOD FOR LARGE-SCALE DAMAGE OF FERROMAGNETIC MATERIALS BASED ON BROADBAND EXCITATION

(71) Applicant: BEIJING UNIVERSITY OF TECHNOLOGY, Beijing (CN)

(72) Inventors: Jingpin Jiao, Beijing (CN); Wenyuan Liang, Beijing (CN); Cunfu He, Beijing (CN); Bin Wu, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 0 days.

(21) Appl. No.: 17/055,599

(22) PCT Filed: Apr. 29, 2020

(86) PCT No.: PCT/CN2020/087683
§ 371 (c)(1),
(2) Date: Nov. 15, 2020

(87) PCT Pub. No.: WO2020/259070
PCT Pub. Date: Dec. 30, 2020

(65) Prior Publication Data
US 2021/0262983 A1     Aug. 26, 2021

(30) Foreign Application Priority Data

Jun. 25, 2019    (CN) .......................... 201910552740.9

(51) Int. Cl.
*G01N 27/82*     (2006.01)
*G01N 33/2045*    (2019.01)

(52) U.S. Cl.
CPC ......... *G01N 27/82* (2013.01); *G01N 33/2045* (2019.01)

(58) Field of Classification Search
None
See application file for complete search history.

(56) References Cited

U.S. PATENT DOCUMENTS 10,466,206 B2\* 11/2019 Vinogradov ....... G01N 29/2412
2009/0193936 A1    8/2009 Lu et al.
2010/0259252 A1\* 10/2010 Kim ..................... H01F 7/0273
                                                  324/240

FOREIGN PATENT DOCUMENTS

CN        105092696 A     11/2015
CN        105353030 A      2/2016
(Continued)

OTHER PUBLICATIONS

Cunfu H, Yuegang H, Jingpin J, et al. "Array of Fundamental Torsional Mode EMATs and Experiment in Thick-wall Pipe with Small Diameter" [J]. Journal of Mechanical Engineering, 2015, 51(2):14-20.

(Continued)

*Primary Examiner* — Matthew G Marini
(74) *Attorney, Agent, or Firm* — Leonid Kisselev

(57) ABSTRACT

The invention discloses a low-frequency electromagnetic detection method for large-scale damage of ferromagnetic materials based on broadband excitation. Detection direction of the magnetic field signal of low-frequency electromagnetic sensor is determined according to the size of ferromagnetic member detection defect; the reference signal and detection signal acquisition position are selected, fix the distance between sensor and tested part, excite a Chirp signal as a broadband excitation signal to perform broadband excitation low-frequency electromagnetic detection; the computer processes collected broadband detection signal; use the difference of Euclidean distance between reference signal and defect detection signal as a defect characterization parameter to obtain the Euclidean distance curve (Continued)

of different depth defects on the upper and lower surfaces of ferromagnetic components with the detection position. Through the analysis and processing of the low-frequency electromagnetic broadband detection signal, the Euclidean response signal and reference signal under broadband excitation are used to characterize the change of material damage degree, which can effectively reduce the influence of magnetic field skin effect, and is beneficial to the effective characterization of the upper and lower material surface defects of at different depths.

3 Claims, 3 Drawing Sheets

(56) References Cited

FOREIGN PATENT DOCUMENTS

| CN | 110196276 A | 9/2019 |
|----|-------------|--------|
| JP | 6447944 A | 2/1989 |
| JP | 2001013111 A | 1/2001 |

OTHER PUBLICATIONS

Wang Z, Luo Q, Shi Y, et al. "Analysis of eddy current coil coupling in ferromagnetic pipe and pipe's parameter detection" [J]. Yi Qi Yi Biao Xue Bao/Chinese Journal of Scientific Instrument, 2014, 35(12):2843-2851.

Sharatchandra Singh W, Rao BP C, Vaidyanathan S, et al. "Detection of leakage magnetic flux from near-side and far-side defects in carbon steel plates using a giant magneto-resistive sensor" [J]. Measurement Science & Technology, 2008, 19(1):1-8.

Sun Y, Feng B, Liu S, et al. "A Methodology for Identifying Defects in the Magnetic Flux Leakage Method and Suggestions for Standard Specimens" [J]. Journal of Nondestructive Evaluation, 2015, 34(20):1-9.

Ying T, Mengchun P, Feilu L, et al. "Detection of Corrosion in Pipeline Using Pulsed Magnetic Flux Leakage Testing" [J]. Computer Measurement & Control, 2010, 18(1):38-43.

Gotoh Y, Takahashi N. "Study on problems in detecting plural cracks by alternating flux leakage testing using 3D nonlinear eddy current analysis" [J]. IEEE Transactions on Magnetics, 2003, 39(3): 1527-1530.

Singh W S, Rao BP C, Thirunavukkarasu S, et al. "Flexible GMR sensor array for magnetic flux leakage testing of steel track ropes" [J]. Journal of Sensors, 2012(2012): 1-6.

Singh W S, Rao B P C, Jayakumar T, et al. "Simultaneous measurement of tangential and normal component of leakage magnetic flux using GMR sensors" [J]. Journal of Non-Destructive Testing & Evaluation, 2009, 8(2): 23-28. [0058].

Jingpin J, Yu C, Guanghai L, et al. "Study on low frequency AC magnetic flux leakage detection for internal and external cracks of ferromagnetic structures" [J]. Chinese Journal of Scientific Instrument, 2016, 37(8):1808-1818.

Hosseini S, Lakis A. A. "Application of time-frequency analysis for automatic hidden corrosion detection in a multilayer aluminum structure using pulsed eddy current" [J]. Ndt & E International, 2012, 47(2):70-79.

* cited by examiner

LOW-FREQUENCY ELECTROMAGNETIC DETECTION METHOD FOR LARGE-SCALE DAMAGE OF FERROMAGNETIC MATERIALS BASED ON BROADBAND EXCITATION

CROSS REFERENCE TO RELATED APPLICATION

This application is a national stage application of International application number PCT/CN2020/087683, filed Apr. 29, 2020, titled "A Low-Frequency Electromagnetic Detection Method For Large-Scale Damage Of Ferromagnetic Materials Based On Broadband Excitation", which claims the priority benefit of Chinese Patent Application No. 201910552740.9, filed on Jun. 25, 2019, which is hereby incorporated by reference in its entirety.

TECHNICAL FIELD

The invention relates to a ferromagnetic material damage detection method, in particular to a low-frequency electromagnetic detection method for large-scale damage of ferromagnetic materials based on broadband excitation. The method is suitable for large-scale damage detection of ferromagnetic materials and belongs to the field of non-destructive testing.

BACKGROUND

Ferromagnetic materials are widely used in aerospace, power, chemical and other fields because of their high strength, good plasticity, impact resistance, and reliable performance. In the process of using these materials, various damages such as cracks and corrosion are easily generated in the uneven and loose areas of the structure under the combined action of fatigue load, internal working medium and external environmental factors, which endanger the safe operation of the structure. Therefore, in order to ensure the normal operation of ferromagnetic components and prevent the occurrence of malignant accidents, it is necessary to develop effective methods for detecting damage to the inner and outer surfaces of ferromagnetic components.

Aiming at the non-destructive testing of ferromagnetic components, the upper and lower surface defects can be detected based on a variety of testing principles, such as acoustics, optics, and electromagnetics. Among them, the detection technology based on electromagnetic principle has special advantages in non-destructive testing of ferromagnetic components. For example, based on the principle of electromagnetic ultrasound, Cunfu H [1] developed a single-mode electromagnetic acoustic sensor in ferromagnetic pipelines, and used the excited single longitudinal or torsional mode guided waves to detect cracks in the pipeline. Due to the extremely complex propagation of ultrasonic guided waves in the pipeline, especially its multi-mode and frequency dispersion characteristics, the development and signal analysis of single-mode electromagnetic sensors are difficult, which limits the practical application of this method in ferromagnetic components; Eddy current technology is also a commonly used electromagnetic nondestructive testing technology for ferromagnetic components. Wang Z[2] obtained the decoupling degree parameter that affects the mutual inductance of eddy current coils during ferromagnetic pipeline testing through coupling analysis of ferromagnetic pipelines and near-field eddy current coils, and verify the effectiveness of this parameter in detecting ferromagnetic pipeline defects by simulation and experiment. However, due to the skin effect, eddy current testing cannot be used to detect defects on the lower surface of ferromagnetic components; in addition, the magnetic flux leakage method is also a commonly used electromagnetic nondestructive testing technology for ferromagnetic components. According to the different excitation methods, the magnetic flux leakage detection technology can be divided into DC magnetic flux leakage method and AC magnetic flux leakage method. In terms of DC magnetic flux leakage detection, Sharatchandra Singh W et al. [3] applied a DC current to the excitation coil and used a giant magnetoresistance GMR sensor as a detector to detect defects in ferromagnetic components at different locations. The test results show that the sensor can effectively detect and locate defects on the front and back of the board. However, DC magnetic flux leakage detection method is greatly affected by the scanning speed and stability. In terms of AC magnetic flux leakage, Yanhua Sun et al. [4] studied the relationship between magnetic flux leakage detection signal characteristic parameters and defects through simulation and experiments. The results show that the peak direction of the two defect detection signals, concave and convex, is opposite to the concave and convex direction of the defect. Under the condition of pulse AC magnetization, Ying T et al. [5] studied the detection ability of the two parameters of detection signal amplitude and zero crossing point on the surface and near surface defects of ferromagnetic components. The results show that, compared with traditional magnetic flux leakage detection, this method can still detect defects on the surface and near the surface of specimen under large lift-off. The existing AC magnetic flux leakage detection frequency is mainly concentrated in high frequency (kHz), and the magnetic flux leakage detection effect is greatly affected by the skin effect, and it is difficult to realize the damage detection of the lower surface of ferromagnetic member.

On the basis of eddy current detection technology and magnetic flux leakage detection technology, low-frequency electromagnetic detection technology was born. Low-frequency electromagnetic detection technology is widely used because of its low detection frequency, less affected by the skin effect, small detection equipment, flexible scanning and rich detection signals. Yuji Gotoh et al. [6] applied the finite element method to numerically simulate the low-frequency electromagnetic field distribution, using AC signal excitation with a frequency lower than 1 kHz, and the detected leakage magnetic field signal can identify the 0.5 mm wide crack defect on the surface of the steel plate. Singh W S et al. [7, 8] used characteristic parameters of detection signal amplitude to realize the quantitative characterization of axial and radial artificial grooves and wear defects. Under the condition of AC sine excitation field, Yu, C et al. [9] studied the detection ability of two characteristic parameters of detection signal amplitude and phase to different depths of upper and lower surface defects. The results show that the phase characteristic parameters are more sensitive to the bottom surface defects. Saleh Hosseini et al. [10] realized the effective detection and classification of buried defects in the multilayer board structure by extracting the impedance value in the detection signal. In summary, domestic and foreign researchers have carried out fruitful research on low-frequency electromagnetic detection technology, but the above-mentioned detection methods are more sensitive to surface and near surface defects of the tested part, and have limited detection capabilities for lower surface defects with large buried depth. Further research in this area is needed.

Aiming at the problem of ferromagnetic material damage detection, the present invention proposes a low-frequency electromagnetic detection technology based on broadband excitation, which solves the problem of large-scale damage detection in ferromagnetic components with a certain thickness. The invention applies broadband excitation to the tested component, so that the penetration depth of magnetic field in the test piece is increased, and the influence of the skin effect on damage detection is reduced. At the same time, the present invention uses similarity between the electromagnetic response signal and the reference signal under wide-band excitation as a characteristic parameter for damage characterization in the structure.

SUMMARY

The purpose of the present invention is to provide a large-scale damage detection method for ferromagnetic materials, especially a low-frequency electromagnetic damage detection method based on broadband excitation. Under the condition that the background magnetic field and the nonlinear effect of the system are small, this method uses broadband signal for excitation. The invention co-opted signal similarity analysis method used in ultrasonic detection signal processing under broadband excitation, and uses Euclidean distance between electromagnetic response signal and reference signal as defect characteristic parameters to realize the characterization of ferromagnetic material damage.

The present invention proposes a low-frequency electromagnetic detection method for large-scale damage of ferromagnetic materials based on broadband excitation, and its basic principles are:

Low-frequency electromagnetic detection is affected by the skin effect, magnetic field in test piece is non-uniformly distributed, and detection ability of buried defects on the lower surface is limited. In order to achieve effective detection of embedded defects in ferromagnetic components, this method establishes a theoretical calculation model for low-frequency electromagnetic detection magnetic fields at different frequencies based on the theory of magnetic dipoles. On this basis, A low-frequency electromagnetic detection method for large-scale damage of ferromagnetic materials based on broadband excitation is developed.

When there are defects such as holes, cracks, pits, etc. in the magnetized ferromagnetic component, magnetic field lines will leak on the two side walls of the defect, resulting in a leakage magnetic field. The magnetic dipole theory believes that the leakage magnetic field of the defect is generated by dipoles of opposite polarity. The directional defects (such as cracks) are assumed to be a infinitely long rectangular groove and perpendicular to the direction of the magnetization field H. In the magnetic flux leakage test, spontaneous magnetization of ferromagnetic material magnetic domain is uniformly distributed on the two side walls of groove in the form of magnetic charge. Assuming that the area density of magnetic charge is Q, the signs of magnetic charges on both sides are opposite. At this time, the influence of defect length can be ignored. Theoretical formula of defect two-dimensional magnetic dipole model shown in FIG. 1 is:

$$H_x(x, y) = \frac{Q}{4\pi\mu_0} \left\{ \int_{-h_2}^{-h_1} \frac{(x+w)dy'}{\left[(x+w)^2 + (y-y')^2\right]^{3/2}} - \int_{-h_2}^{-h_1} \frac{(x-w)dy'}{\left[(x-w)^2 + (y-y')^2\right]^{3/2}} \right\} \quad (1)$$

$$H_y(x, y) = \frac{Q}{4\pi\mu_0} \left\{ \int_{-h_2}^{-h_1} \frac{(y-y')dy'}{\left[(x+w)^2 + (y-y')^2\right]^{3/2}} - \int_{-h_2}^{-h_1} \frac{(y-y')dy'}{\left[(x-w)^2 + (y-y')^2\right]^{3/2}} \right\} \quad (2)$$

Wherein, Hx represents the tangential magnetic field intensity, Hy represents the normal magnetic field intensity, x represents the abscissa of the observation point P, y represents the ordinate of the observation point P, $\mu_0$ represents the permeability of the vacuum permeability, and $h_1$ represents the upper surface of the defect buried depth, $h_2$ represents the buried depth of the bottom surface, w represents half of the defect width, and y' represents the distance from left and right groove wall micro-line elements dy to the material surface.

The principle of low-frequency electromagnetic detection is similar to that of magnetic flux leakage detection, but the magnetization method of low-frequency electromagnetic detection uses an alternating magnetic field. Therefore, the distribution of magnetic lines of force in the test piece presents a skin effect similar to the distribution of induced current density in eddy current testing, that is, the skin depth becomes shallower with the increase of excitation frequency [11]. Therefore, in low-frequency electromagnetic testing, relationship between magnetic charge density at depth h below the surface of test piece and its surface magnetic charge density can be approximately expressed as:

$$\frac{Q_h}{Q_0} = e^{-h\sqrt{\pi f \mu \sigma}} \quad (3)$$

Wherein, $Q_h$ represents the magnetic charge density at distance h from the component surface, $Q_0$ represents the magnetic charge density at the component surface, σ represents the permeability of ferromagnetic material, ii represents the conductivity of ferromagnetic material, and f represents the excitation signal frequency. Introduce low-frequency electromagnetic detection magnetic field skin formula (3) into magnetic dipole models (1) and (2) to obtain equivalent magnetic dipole model for low-frequency electromagnetic detection:

$$H_x(x, y, f) = \quad (4)$$

$$\frac{Q_0}{4\pi\mu_0} \left\{ \int_{-h_2}^{-h_1} \frac{e^{-y'\sqrt{\pi f \mu \sigma}}(x+w)dy'}{\left[(x+w)^2 + (y-y')^2\right]^{3/2}} - \int_{-h_2}^{-h_1} \frac{e^{-y'\sqrt{\pi f \mu \sigma}}(x-w)dy'}{\left[(x-w)^2 + (y-y')^2\right]^{3/2}} \right\}$$

$$H_y(x, y, f) = \quad (5)$$

$$\frac{Q_0}{4\pi\mu_0} \left\{ \int_{-h_2}^{-h_1} \frac{e^{-y'\sqrt{\pi f \mu \sigma}}(y-y')dy'}{\left[(x+w)^2 + (y-y')^2\right]^{3/2}} - \int_{-h_2}^{-h_1} \frac{e^{-y'\sqrt{\pi f \mu \sigma}}(y-y')dy'}{\left[(x-w)^2 + (y-y')^2\right]^{3/2}} \right\}$$

It can be seen from formulas (4) and (5) that the magnetic charge density of low-frequency electromagnetic detection is no longer uniformly distributed with the increase of defect depth, but with an exponential decay trend. At this time, the tangential magnetic field $H_x$ and the normal magnetic field $H_y$ generated by the defect at the observation point P(x,y) are functions of the frequency f, which are consistent with the principle of low-frequency electromagnetic detection.

Low-frequency electrical testing is affected by the skin effect. When the excitation signal is a single-frequency signal, the effective detection magnetic field distribution range in test piece is narrow, which is not conducive to the detection of buried defects at different depths. In order to realize effective detection of buried defects on the inner and lower surfaces of ferromagnetic components, this method study the low-frequency electromagnetic detection method for large-scale damage of ferromagnetic materials under broadband excitation based on low-frequency electromagnetic equivalent magnetic dipole model.

In the broadband excitation low-frequency electromagnetic detection method, excitation signal is a broadband signal, and the corresponding detection signal is also a broadband signal. Therefore, amplitude and phase parameters under conventional single-frequency excitation cannot fully reflect the information contained in detection signal. Taking signal similarity analysis method used in processing of ultrasonic detection signals under broadband excitation as reference, the broadband excitation response of reference area is used as reference signal, and the broadband response of detection signal is analyzed for similarity. The broadband response Euclidean distance is used as the characteristic parameter. For defects characterization on the upper and lower surfaces of ferromagnetic components, calculation process of the Euclidean distance characterization parameter is shown in FIG. 2. The Euclidean distance characterization parameter $E(H_d, H_n)$ can be calculated by formula (6):

$$E(H_d, H_n) = \sqrt{(\Sigma(H_{di} - H_{ni})^2)} \quad (6)$$

Wherein, $H_d$ represents magnetic field strength of the area to be detected, $H_n$ represents the reference magnetic field strength of the reference area, $H_{di}$ represents the magnetic field strength of the area to be detected at each frequency, and $H_{ni}$ represents the reference magnetic field strength of the reference area at each frequency.

Compared with traditional low-frequency electromagnetic detection method, broadband excitation low-frequency electromagnetic detection method has a wider excitation signal frequency band and a wider magnetic field distribution in the test piece, which is conducive to the detection of different depth defects. The Euclidean distance characterization parameter can obtain the difference between defect detection signal and non-defect reference signal at different frequencies, which can avoid mismatch between magnetic field penetration depth and defect buried depth, and realize effective detection of upper and lower surface defects at different depths.

The technical scheme of the present invention is as follows:

The device used in the present invention is shown in FIG. 3, including a function generator 1, a power amplifier 2, a digital oscilloscope 3, a stabilized current power supply 4 and a low-frequency electromagnetic sensor 5. First, divide the output port of the function generator 1 into two channels, one connected to the second channel of digital oscilloscope 3 for displaying broadband excitation signals, and the other connected to the input port of the power amplifier 2 for magnetizing DUT. Then, output end of the power amplifier 2 is connected to the input end of the low-frequency electromagnetic sensor 5, and its output end is connected to the first channel of the digital oscilloscope 3 for displaying the electromagnetic signal detected by the low-frequency electromagnetic sensor 5. Finally, the positive and negative poles of stabilized current power supply 4 are respectively connected to the two power supply input terminals of low-frequency electromagnetic sensor 5 for supplying the power for magnetic sensor inside low-frequency electromagnetic sensor 5.

The present invention proposes a low-frequency electromagnetic detection method for large-scale damage of ferromagnetic materials based on broadband excitation, which is implemented through the following steps:

A piece of ferromagnetic steel plate commonly used in industry is selected as a test piece. The thickness of ferromagnetic steel plate is between 12 mm-16 mm. There are crack defects of different depths on the surface of ferromagnetic steel plate. Each crack defect has the same dimensions except for the depth. The maximum depth is less than the thickness of ferromagnetic steel plate;

Adjust a signal pickup direction of a magnetic sensor inside a low-frequency electromagnetic sensor to make the detection direction parallel to the surface of the test piece. At this time, the detection result is strength of the tangential leakage magnetic field on the surface of ferromagnetic steel plate. Magnetic field strength in this direction is sensitive to the depth of defect;

Arrange the test piece as shown in FIG. 4a, place low-frequency electromagnetic sensor on the surface of the test plate so that it is in the defect-free reference area of the ferromagnetic steel plate, and adjust the lift-off distance between low-frequency electromagnetic sensor and the test piece to be less than 1 mm.

Adjust a function generator to generate Chirp signal with fixed output voltage and bandwidth for excitation, and activate a power amplifier. The digital oscilloscope will simultaneously display the excitation signal and electromagnetic detection signal of the low-frequency electromagnetic sensor in defect-free reference area of the ferromagnetic steel plate. The detected signal is used as a reference signal for no defect and saved;

Place the low-frequency electromagnetic sensor at one side of the crack, and under the same excitation conditions, manually control the moving direction of the low-frequency electromagnetic sensor so that the moving direction is perpendicular to the length of the crack under test. Activate the power amplifier. Whenever the low-frequency electromagnetic sensor is placed at a detection point, digital oscilloscope will simultaneously display the excitation signal and electromagnetic detection signal of the low-frequency electromagnetic sensor at the detection point, collect the broadband detection signals of all detection points as defect detection signals;

Collected reference signals and defect detection signals are processed by computer. First, perform frequency domain analysis on reference signal and each defect detection signal to obtain the reference signal spectrum and the defect detection signal spectrum at different positions. Then, Euclidean distance calculation formula (6) is used to obtain frequency domain Euclidean distance between detection signal and reference signal at each detection point. Using the frequency domain Euclidean distance as defect characteristic parameter to draw the curve of Euclidean distance versus detection position;

Arrange the tested piece as shown in FIG. 4b, repeat steps 3) to 6), and obtain the curve of Euclidean distance with detection position when defect is located on the lower surface of the tested piece;

Based on Euclidean distance curve, the upper and lower surface defects of ferromagnetic components at different depths are quantitatively characterized.

When the sensor moving speed and direction are known, crack position can also be located.

The invention has the following advantages: (1) Broadband signals are used for excitation, magnetic field is distributed in a wide range in the tested piece, the detection is less affected by skin effect, and the penetration depth of low-frequency electromagnetic detection magnetic field is more than 12 mm, which can be used for iron Detection of buried defects on the lower surface of magnetic component; (2) Using Euclidean distance as defect characterization parameter, the difference between defect detection signal and non-defect reference signal at different frequencies can be obtained to avoid the problem of mismatch between magnetic field penetration depth and defect buried depth. Realizing effective detection of upper and lower surface defects at different depths.

Through the analysis and processing of low-frequency electromagnetic broadband detection signals, Euclidean distance between electromagnetic response signal and reference signal is used to characterize the change in degree of material damage, which can effectively reduce the influence of magnetic field skin effect, and is beneficial to the effective characterization of the upper and lower surface defects of material at different depths.

DETAILED DESCRIPTION OF THE PREFERRED EMBODIMENTS

Figure 1:
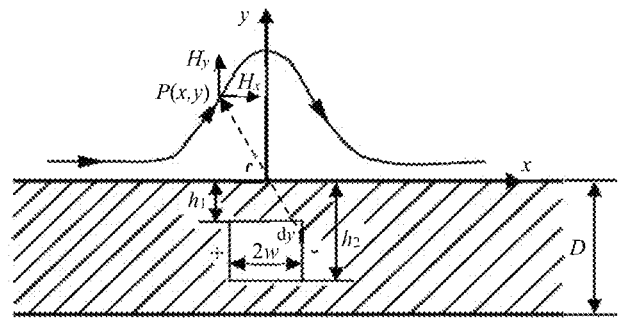
FIG. 1 is a cross-sectional view of a rectangular slot two-dimensional magnetic dipole model.
Figure 2:
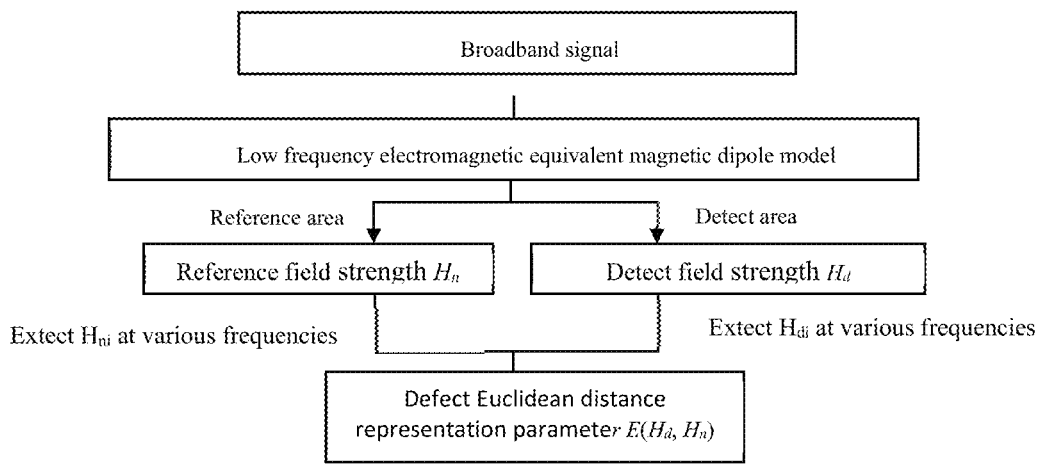
FIG. 2 is a Euclidean distance defect characterization flowchart.
Figure 3:
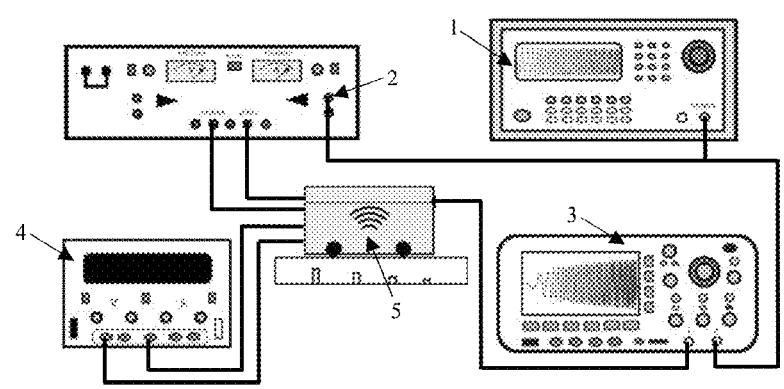
FIG. 3 is a low-frequency electromagnetic detection system diagram; wherein: 1. Function generator, 2. Power amplifier, 3. Digital oscilloscope, 4. Stabilized current power supply, 5. Low frequency electromagnetic sensor.

The present invention will be further described below in conjunction with preferred embodiment:

The implementation process includes the following steps:
Construction of the Experimental System:

The system used in the present invention is built based on in FIG. 3, including a function generator 1, a power amplifier 2, a digital oscilloscope 3, a stabilized current power supply 4 and a low-frequency electromagnetic sensor 5. First, divide the output port of the function generator 1 into two channels, one connected to the second channel of digital oscilloscope 3 for displaying broadband excitation signals, and the other connected to the input port of the power amplifier 2 for magnetizing DUT. Then, output end of the power amplifier 2 is connected to the input end of the low-frequency electromagnetic sensor 5, and its output end is connected to the first channel of the digital oscilloscope 3 for displaying the electromagnetic signal detected by the low-frequency electromagnetic sensor 5. Finally, the positive and negative poles of stabilized current power supply 4 are respectively connected to the two power supply input terminals of low-frequency electromagnetic sensor 5 for supplying the power for magnetic sensor inside low-frequency electromagnetic sensor 5.

Magnetic sensor detection direction selection: the test piece is 20# low carbon steel plate, a 620×400×12 mm commonly used ferromagnetic material. The steel plate has four standard artificial defects with 25 mm long and 4 mm wide, the depth of these four defects are 4.8 mm, 6.0 mm, 7.2 mm and 9.6 mm. Since the width of the defect is equal and depth is different, the detection direction of magnetic sensor is adjusted to be parallel to the tangential direction on the surface of tested steel plate, so that the electromagnetic detection signal is more sensitive to depth.

Sensor parameter selection: Place the sensor on defect-free side and defective side of the tested steel plate surface, manually control the sensor to maintain a lift-off distance of 1 mm from steel plate surface. Adjust the function generator, set excitation signal to a broadband Chirp signal, control the voltage to 3V, and the frequency bandwidth to 0-150 Hz.

Figures 4A, 4B:
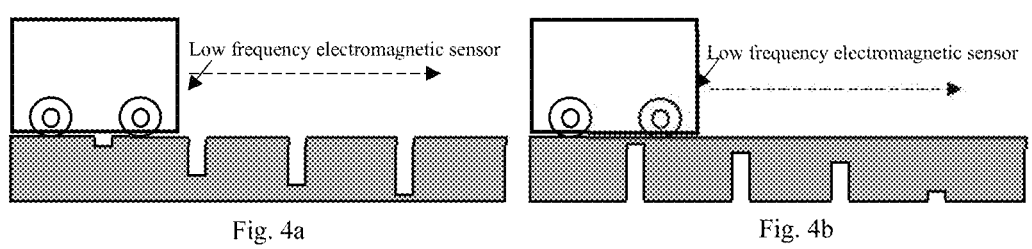
FIG. 4a is a schematic diagram of upper surface defects scanning and detecting.
FIG. 4b is a schematic diagram of lower surface defects scanning and detecting.

Electromagnetic testing experiment: Place the sensor in non-defective reference area, turn on the power amplifier, and use digital oscilloscope to record and collect the non-defective reference signal. According to FIG. 4a and FIG. 4b, select a 30 mm linear distance perpendicular to the length of defect to make the sensor moves from left to right within the selected linear distance during detect. The detection step length is controlled to 1 mm, and the detection speed changes manually. Use digital oscilloscope to record the excitation signal and electromagnetic detection signal of a single position, and store the defect detection signal of 31 points during movement.

Figure 5A:
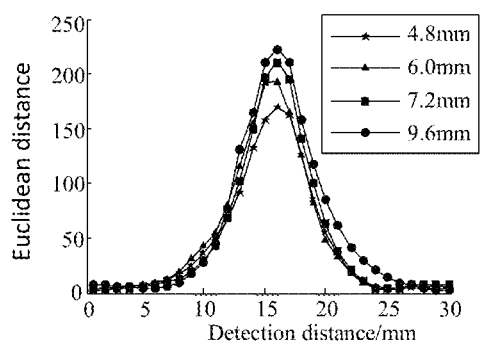
FIG. 5a is diagram showing characterization results of broadband Euclidean distance on the upper surface defect.
Figure 5B:
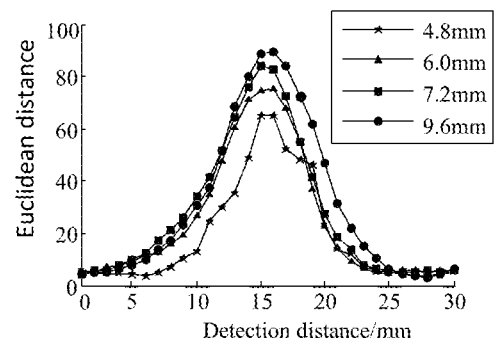
FIG. 5b is a diagram showing characterization results of broadband Euclidean distance on the lower surface defect.

The computer processes the collected reference signals and the defect detection signals. First, perform frequency domain analysis on the reference signal and each detection signal to obtain reference signal spectrum and detection signal spectrum at different positions. Then Euclidean distance calculation formula (6) is used to obtain the frequency domain Euclidean distance between detection signal and reference signal at each detection point, and the distance is used as the defect characteristic parameter to draw the curve of Euclidean distance of the surface defect at different depths with the detection position (As shown in FIG. 5a) and the curve of the Euclidean distance between the lower surface defects and the detection position (as shown in FIG. 5b).

Analysis of experimental results: the depth of each defect and the position of the defect is known. It can be seen from FIG. 5a and FIG. 5b that the peaks in two figures can be judged, and the application of broadband excitation low-frequency electromagnetic detection method can effectively distinguish different depth defects on the upper and lower surfaces of steel plate. For four defects with equal width and different depth, the Euclidean distance detection amplitude on the upper surface is 169.2, 193.0, 212.4, 224.3; the Euclidean distance detection amplitude on the lower surface is 65.36, 75.11, 84.38, 89.33. The detection amplitude of each defect on the upper and lower surfaces is quite different, and the defect separation rate is higher.

While the invention has been particularly shown and described as referenced to the embodiments thereof, those skilled in the art will understand that the foregoing and other changes in form and detail may be made therein without departing from the spirit and scope of the invention.

REFERENCE

[1] Cunfu H, Yuegang H, Jingpin J, et al. Array of Fundamental Torsional Mode EMATs and Experiment in Thick-wall Pipe with Small Diameter[J]. Journal of Mechanical Engineering, 2015, 51(2):14-20.

[2] Wang Z, Luo Q, Shi Y, et al. Analysis of eddy current coil coupling in ferromagnetic pipe and pipe's parameter detection[J]. Yi Qi Yi Biao Xue Bao/Chinese Journal of Scientific Instrument, 2014, 35(12):2843-2851.

[3] Sharatchandra Singh W, Rao B P C, Vaidyanathan S, et al. Detection of leakage magnetic flux from near-side and far-side defects in carbon steel plates using a giant magneto-resistive sensor[J]. Measurement Science & Technology, 2008, 19(1):1-8.

[4] Sun Y, Feng B, Liu S, et al. A Methodology for Identifying Defects in the Magnetic Flux Leakage Method and Suggestions for Standard Specimens[J]. Journal of Nondestructive Evaluation, 2015, 34(20):1-9.

[5] Ying T, Mengchun P, Feilu L, et al. Detection of Corrosion in Pipeline Using Pulsed Magnetic Flux Leakage Testing[J]. Computer Measurement & Control, 2010, 18(1):38-43.

[6] Gotoh Y, Takahashi N. Study on problems in detecting plural cracks by alternating flux leakage testing using 3D nonlinear eddy current analysis[J]. IEEE Transactions on Magnetics, 2003, 39(3): 1527-1530.

[7] Singh W S, Rao B P C, Thirunavukkarasu S, et al. Flexible GMR sensor array for magnetic flux leakage testing of steel track ropes[J]. Journal of Sensors, 2012 (2012): 1-6.

[8] Singh W S, Rao B P C, Jayakumar T, et al. Simultaneous measurement of tangential and normal component of leakage magnetic flux using GMR sensors[J]. Journal of Non-Destructive Testing & Evaluation, 2009, 8(2): 23-28.

[9] Jingpin J, Yu C, Guanghai L, et al. Study on low frequency AC magnetic flux leakage detection for internal and external cracks of ferromagnetic structures[J]. Chinese Journal of Scientific Instrument, 2016, 37(8):1808-1818.

[10] Hosseini S, Lakis A A. Application of time-frequency analysis for automatic hidden corrosion detection in a multilayer aluminum structure using pulsed eddy current [J]. Ndt & E International, 2012, 47(2):70-79.

What is claimed is:

1. A low-frequency electromagnetic detection method for large-scale damage of ferromagnetic materials based on broadband excitation, comprising the steps of:
   1) selecting a piece of ferromagnetic steel plate as a test piece, the ferromagnetic steel plate comprising a surface and an another surface, wherein a thickness of the ferromagnetic steel plate is between 12 mm-16 mm, wherein the surface and the another surface of the ferromagnetic steel plate comprise crack defects of different depths and wherein all of the crack defects have same dimensions except for depth and wherein a maximum one of the depths is less than the thickness of the ferromagnetic steel plate;
   2) adjusting a detection direction of a magnetic sensor inside a low-frequency electromagnetic sensor to make the detection direction parallel to the surface of the test piece, wherein a result of the detection result comprises tangential leakage magnetic field strength on the surface of the test piece, wherein magnetic field strength in this direction depends on the defect depth;
   3) placing the low-frequency electromagnetic sensor on the surface of the ferromagnetic steel plate so that the low-frequency electromagnetic sensor is in a reference area of the ferromagnetic steel plate that is free of the crack defects, and adjusting a lift-off distance between the low-frequency electromagnetic sensor and the ferromagnetic steel plate to be less than 1 mm;
   4) obtaining a reference signal, comprising:
      adjusting a function generator, the function generator interfaced to a digital oscilloscope and to a power amplifier, to generate an excitation signal comprising a Chirp signal with fixed output voltage and bandwidth for excitation, and activating the power amplifier interfaced to the low-frequency electromagnetic sensor, wherein the low-frequency electromagnetic sensor is interfaced to the digital oscilloscope;
      simultaneously displaying on the digital oscilloscope the excitation signal and an electromagnetic detection signal detected by the low-frequency electromagnetic sensor at the defect-free reference area of the ferromagnetic steel plate;
      assigning the electromagnetic detection signal as the reference signal;
   5) obtaining defect detection signals, comprising:
      placing the low-frequency electromagnetic sensor at one side of one of the crack defects;
      manually controlling a direction the low-frequency electromagnetic sensor is moved along a plurality of detection points so that the moving direction is perpendicular to a longitude of the one crack defect;
      whenever the low-frequency electromagnetic sensor is placed at one of the detection points, applying the excitation signal to the test piece while simultaneously displaying on the digital oscilloscope the excitation signal and electromagnetic detection signal detected by the low-frequency electromagnetic sensor at that detection point;
      assigning the electromagnetic detection signals collected at all of the detection points as the defect detection signals;
   6) processing the collected reference signal and defect detection signals via a computer, comprising:
      performing frequency domain analysis on reference signal and each defect detection signal to obtain a spectrum of the reference signal spectrum and a spectrum of the defect detection signal at different ones of the detection points;
      using Euclidean distance calculation formula to obtain a frequency domain Euclidean distance between the detection signal at each detection point and the reference signal;
      using the frequency domain Euclidean distance as a defect characteristic parameter to draw a curve of Euclidean distance versus detection position;
   7) flipping the test piece and repeating the steps 3) to 6) on the another surface of the test piece comprising obtaining a further curve of Euclidean distance versus detection position based on one or more of the crack defects appearing below the another surface of the test piece; and
   8) quantitatively characterizing the crack defects at different depths of the ferromagnetic steel plate based on the Euclidean distance curve and the further Euclidian distance curve, wherein an industrial use of the ferromagnetic steel plate is based on the characterization.

2. A low-frequency electromagnetic detection method for large-scale damage of ferromagnetic materials based on broadband excitation according to claim 1, further comprising:

establishing a theoretical calculation model for low-frequency electromagnetic detection magnetic fields at different frequencies based on a theory of magnetic dipoles, comprising:

setting a formula for two dimensional magnetic dipole model associated with surface defects in a magnetized ferromagnetic material in a magnetization field H and the area density of magnetic charge is Q in accordance with:

$$H_x(x,y) = \frac{Q}{4\pi\mu_0}\left\{\int_{-h_2}^{-h_1}\frac{(x+w)dy'}{\left[(x+w)^2+(y-y')^2\right]^{3/2}} - \int_{-h_2}^{-h_1}\frac{(x-w)dy'}{\left[(x-w)^2+(y-y')^2\right]^{3/2}}\right\} \quad (1)$$

$$H_y(x,y) = \frac{Q}{4\pi\mu_0}\left\{\int_{-h_2}^{-h_1}\frac{(y-y')dy'}{\left[(x+w)^2+(y-y')^2\right]^{3/2}} - \int_{-h_2}^{-h_1}\frac{(y-y')dy'}{\left[(x-w)^2+(y-y')^2\right]^{3/2}}\right\} \quad (2)$$

wherein, Hx represents a tangential magnetic field intensity, Hy represents a normal magnetic field intensity, x represents an abscissa of an observation point P, y represents an ordinate of the observation point P, $\mu_o$ represents a permeability of a vacuum permeability, and $h_1$ represents an upper surface of a defect buried depth, $h_2$ represents a buried depth of a bottom surface, w represents half of a defect width, and y' represents a distance from left and right groove wall micro-line elements $d_y$, to the material surface;

wherein relationship between magnetic charge density at depth h below the surface of the test piece and surface magnetic charge density of the test piece can be expressed as:

$$\frac{Q_h}{Q_0} = e^{-h\sqrt{\pi f \mu \sigma}} \quad (3)$$

wherein, Qh represents the magnetic charge density at distance h from the test piece surface, $Q_0$ represents the magnetic charge density at the test piece surface, σ represents a permeability of ferromagnetic material, μ represents a conductivity of ferromagnetic material, and f represents an excitation signal frequency, wherein equivalent magnetic dipole model for low-frequency electromagnetic detection is determined in accordance with:

$$H_x(x,y,f) = \quad (4)$$

$$\frac{Q_0}{4\pi\mu_0}\left\{\int_{-h_2}^{-h_1}\frac{e^{-y'\sqrt{\pi f \mu \sigma}}(x+w)dy'}{\left[(x+w)^2+(y-y')^2\right]^{3/2}} - \int_{-h_2}^{-h_1}\frac{e^{-y'\sqrt{\pi f \mu \sigma}}(x-w)dy'}{\left[(x-w)^2+(y-y')^2\right]^{3/2}}\right\}$$

$$H_y(x,y,f) = \quad (5)$$

$$\frac{Q_0}{4\pi\mu_0}\left\{\int_{-h_2}^{-h_1}\frac{e^{-y'\sqrt{\pi f \mu \sigma}}(y-y')dy'}{\left[(x+w)^2+(y-y')^2\right]^{3/2}} - \int_{-h_2}^{-h_1}\frac{e^{-y'\sqrt{\pi f \mu \sigma}}(y-y')dy'}{\left[(x-w)^2+(y-y')^2\right]^{3/2}}\right\}$$

wherein the magnetic charge density of low-frequency electromagnetic detection is not uniformly distributed with the increase of defect depth, but with an exponential decay trend, wherein the Euclidean distance characterization parameter E ($H_d$, $H_n$) can be calculated by formula (6):

$$E(H_d,H_n) = \sqrt{\Sigma(H_{di}-H_{ni})^2} \quad (6)$$

wherein, $H_d$ represents the magnetic field strength of an area to be detected, $H_n$ represents the reference magnetic field strength of the reference area, $H_{di}$ represents the magnetic field strength of the area to be detected at each frequency, and $H_{ni}$ represents the reference magnetic field strength of the reference area at each frequency.

3. A low-frequency electromagnetic detection method for large-scale damage of ferromagnetic materials based on broadband excitation according to claim 1, further comprising:

providing a system that comprises the function generator, the power amplifier, the digital oscilloscope, a stabilized current power supply and the low-frequency electromagnetic sensor;

dividing an output port of the function generator into two channels, one channel connected to a second channel of the digital oscilloscope for displaying broadband excitation signals comprising the excitation signal and the other channel connected to the input port of the power amplifier; and connecting an output end of the power amplifier to an input end of the low-frequency electromagnetic sensor, connecting an output end of the low-frequency electromagnetic sensor to a first channel of the digital oscilloscope for displaying the electromagnetic signal detected by the low-frequency electromagnetic sensor, and positive and negative poles of the stabilized current power supply respectively to two power supply input terminals of low-frequency electromagnetic sensor for supplying power for the magnetic sensor inside the low-frequency electromagnetic sensor.

* * * * *